(12) United States Patent
Brown

(10) Patent No.: US 6,360,590 B1
(45) Date of Patent: Mar. 26, 2002

(54) METHOD AND APPARATUS FOR INVESTIGATING SURFACES

(75) Inventor: Colin W. Brown, Milwaukee, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/485,254

(22) PCT Filed: Aug. 7, 1998

(86) PCT No.: PCT/US98/16482

§ 371 Date: Feb. 7, 2000

§ 102(e) Date: Feb. 7, 2000

(87) PCT Pub. No.: WO99/08093

PCT Pub. Date: Feb. 18, 1999

(30) Foreign Application Priority Data

Aug. 7, 1997 (GB) ............................................. 9716781

(51) Int. Cl.[7] .......................... G01N 19/02; G01N 37/00
(52) U.S. Cl. ................... 73/104; 73/863.22; 73/863.41; 73/863.24; 73/28.01
(58) Field of Search ........................ 73/863.41, 863.22, 73/863.24, 104, 28.01

(56) References Cited

U.S. PATENT DOCUMENTS

| | | |
|---|---|---|
| 2,195,842 A | 4/1940 | Schweickart |
| 3,572,128 A | 3/1971 | Hemeon |
| 3,715,911 A | 2/1973 | Chuan |
| 4,693,173 A * | 9/1987 | Saiki et al. .................. 454/187 |
| 4,979,403 A | 12/1990 | Pike |
| 5,011,900 A * | 4/1991 | Yukimoto et al. .......... 525/477 |
| 5,253,538 A * | 10/1993 | Swick et al. .................. 73/104 |
| 5,421,214 A | 6/1995 | Burgdorfer |
| 5,500,369 A | 3/1996 | Kiplinger |
| 5,502,998 A * | 4/1996 | Miller et al. .................. 73/1.06 |
| 5,553,496 A | 9/1996 | Nishiyama et al. |
| 5,654,205 A * | 8/1997 | Chae et al. ............... 73/28.01 |
| 6,090,875 A * | 7/2000 | Staples et al. .............. 524/313 |

FOREIGN PATENT DOCUMENTS

| | | | |
|---|---|---|---|
| EP | 0754428 A1 | 7/1996 | |
| GB | 2227316 * | 7/1990 | ................ 73/28.01 |
| WO | WO 97/14033 | 4/1997 | |

* cited by examiner

Primary Examiner—Hezron Williams
Assistant Examiner—Michael Cygan

(57) ABSTRACT

A process for comparing the dust retention properties of various treated and untreated hard surfaces, within a dust retaining enclosure, that includes subjecting the surfaces to be compared, previously coated with a standardized layer of dust, to a standardized dust dislodging force sufficient to dislodge dust from at least one of the surfaces, determining any increase in the quantity of dust particles in the atmosphere within the enclosure as a result of the dust dislodging force, and comparing the relative amounts of dust particles found in within the enclosure for the surfaces.

8 Claims, 1 Drawing Sheet

METHOD AND APPARATUS FOR INVESTIGATING SURFACES

TECHNICAL FIELD

The present invention relates to a method and apparatus for investigating the deposition and retention of particulate material on surfaces.

BACKGROUND ART

There have been various proposals for determining the amount of airborne particulate materials present in the air in various environments. Thus U.S. Pat. No. 3,572,128 discloses a polished metal disk exposed to the air on which dust can settle. Periodically all the dust on the surface is wiped off and concentrated by suction in order to determine the quantity of dust deposited.

It is known to treat hard surfaces with products such as furniture polish to clean them and impart desirable properties such as increased shine to the surface. Such surfaces are exposed to airborne dust. Some dust particles may be electrically charged and some products for cleaning hard surfaces claim to reduce the static charge on the surface and so to reduce the tendency of the surface to attract dust. However dust will still be deposited on substantially horizontal surfaces by the action of gravity. The nature of any treatment applied to the surface may affect the strength with which the dust is bound to the surface and its ease of removal in any subsequent cleaning operation. In such a situation the information of primary interest is not the amount of dust in the atmosphere which is deposited over a period of time on the surface but the properties of the dust on the surface.

The applicant has understood that there is a need to be able to compare the effects of different treatments on the ability of a hard surface to retain dust and has provided a method and apparatus for carrying out such comparisons.

DISCLOSURE OF INVENTION

According to the present invention there is provided a process for comparing dust retention properties of a first surface of a substrate with the dust retention properties of a second surface of a substrate,which comprises, within a dust-retaining enclosure, a) subjecting said first surface, previously coated with a standardized layer of dust, to a standardized dust dislodging force sufficient to dislodge dust from at least one of the surfaces.

b) determining any increase in the quantity of dust particles in the atmosphere within the enclosure as a result of the dust dislodging force, c) removing any excess dust particles resulting from the application of the dust dislodging force from the atmosphere in the enclosure, d) subjecting said second surface, previously coated with a standardized layer of dust, to a standardized dust dislodging force, e) determining any increase in the quantity of dust particles in the atmosphere within the enclosure as a result of the dust dislodging force, and f) comparing the relative amounts of dust particles found by steps b) and e).

The applicant has realized that instead of examining the surfaces directly, it is possible to study the atmosphere above the surface, making possible a simple test method using readily available components.

According to a further aspect of the invention there is provided an apparatus suitable for use in comparing the dust retention properties of surfaces, said apparatus comprising a) a dust-retaining enclosure, b) substrate introduction means for introducing a substrate into the enclosure, said substrate having a surface exposed to the atmosphere within the container when within the container, c) manipulation means for allowing manipulation of the substrate within the enclosure from outside the enclosure, d) gas stream means for introducing a stream of gas into the enclosure adjacent to said surface of the substrate when the substrate is within the enclosure, e) dust measurement means for measuring the dust content in the atmosphere within the enclosure.

Preferably, the apparatus also has dust distribution means, said dust distribution means comprising a dust receiving means within the enclosure and air distribution means for passing air over the dust receiving means.

The substrate introduction means may be a portion of the enclosure which may be moved to allow access to the interior of the enclosure.

The manipulation means may be an opening or openings through which an operator's hand can be inserted and which can be blanked off when not required.

The first and second surfaces may be provided on different substrates which are introduced separately into the enclosure with the dust dislodging step being applied separately to each substrate in the absence of the other. Where two substrates are used it is preferred to have both present in the enclosure simultaneously, and for suitable shielding to be provided to protect one substrate while the dust dislodging step is applied to the other.

The present invention may be used to compare the inherent dust retention properties of two different materials, in which case the two surfaces will be the surfaces of two different substrates. The invention may also be used to compare the effects of different surface treatments applied to the same material. In such a case two different substrates of the same material may be used. It may be more convenient to provide the surfaces to be compared on a single substrate.

The optimum area of each surface to be investigated will depend on the size of the enclosure but may for example be in the range 200–1000 $cm^2$, e.g. 600 $cm^2$.

The enclosure used in the method must retain at least a substantial proportion of the dust released from the surfaces under investigation, so that sufficient remains in the atmosphere within the enclosure to be measured. The size of the enclosure is desirably selected in relation to the size of the surface which carries dust so as to give a measurable increase in dust levels within the atmosphere within the enclosure. An enclosure the size of a mobile fume cupboard with a volume of less than 1 cubic metre is suitable.

The surfaces to be compared require to be coated with a standardized layer of dust so that the results for dust displaced into the atmosphere of the enclosure are comparable. This standardized layer may be deposited outside the enclosure. Thus the surfaces to be compared may be left exposed to airborne dust in the same room for the same period of time. It is preferred, however, to deposit the dust layer on the surface after the substrate has been introduced into the enclosure. In order to deposit the dust layer on the substrate within the enclosure it may be desirable to provide the enclosure with a dust receiving means for receiving a sample of dust and air distributing means for passing air over the dust receiving means so as distribute the dust into the air within the enclosure from which it can settle on to the substrate. The air distribution means may be a fan which draws air into the enclosure from outside. The dust receiving means may conveniently be a sieve with a relatively coarse mesh size, greater than the size of the individual dust particles. Because of the tendency of dust to form loosely bound agglomerates the dust will be retained on the sieve to a considerable extent until air is blown on to it by the fan. The sieve helps to provide some turbulence in any air stream directed on to it.

The standardized dust dislodging force may for example be mechanical agitation provided by an object such as a duster coming into contact with the surface carrying the dust. The standardisation may be provided by specifying the nature of the object, the force applied, and the number of times the object is passed over the surface. Where any individual dust dislodging step is likely to be have be variable, as when a human tester uses a duster, a standardized dust dislodging force may be taken to be applied if the average of a sufficient number of individual results are combined to produce the final comparison.

For a more exact application of a standardized dust dislodging force it is preferred to use a stream of gas. The stream of gas, which is most conveniently air, must be such as to be capable of displacing dust from the surface on which the dust is deposited. The gas stream is conveniently produced by a compressor and is conveniently applied by a nozzle close to the surface from which dust is to be displaced. The nozzle may be disposed so as to apply a stream of gas parallel to the surface on which the dust is deposited. Alternatively it may be applied substantially perpendicularly to the surface. The gas stream must not be so weak that no significant amount of dust is displaced from any surface tested, or so strong that all the dust is displaced from all the surfaces tested. Once the inventive idea has been disclosed the skilled person will be able to select gas pressures, nozzle sizes and position relative to the surface, and duration so as to give the optimum discrimination between the surfaces to be tested. By way of example the nozzle may have a diameter of 3 to 10 mm, may be mounted 2–10 mm above the test panel and may be supplied with compressed air at a pressure of 0.5 to 2 bar (gauge).

The amount of dust in the atmosphere within the enclosure may be determined by any convenient method. Apparatus for determining the number of particles of various sizes dispersed in air is commercially available.

The excess dust particles released into the atmosphere of the enclosure by the action of the stream of gas may be removed by allowing them to settle out over a period of time. In such a case it will be necessary to provide a shield for any test surfaces within the enclosure which are awaiting examination in order to prevent this dust settling on them.

BRIEF DESCRIPTION OF DRAWINGS

The invention will now be described with reference to the accompanying drawings in which.

BEST MODE OF CARRYING OUT THE INVENTION

Figure 1:
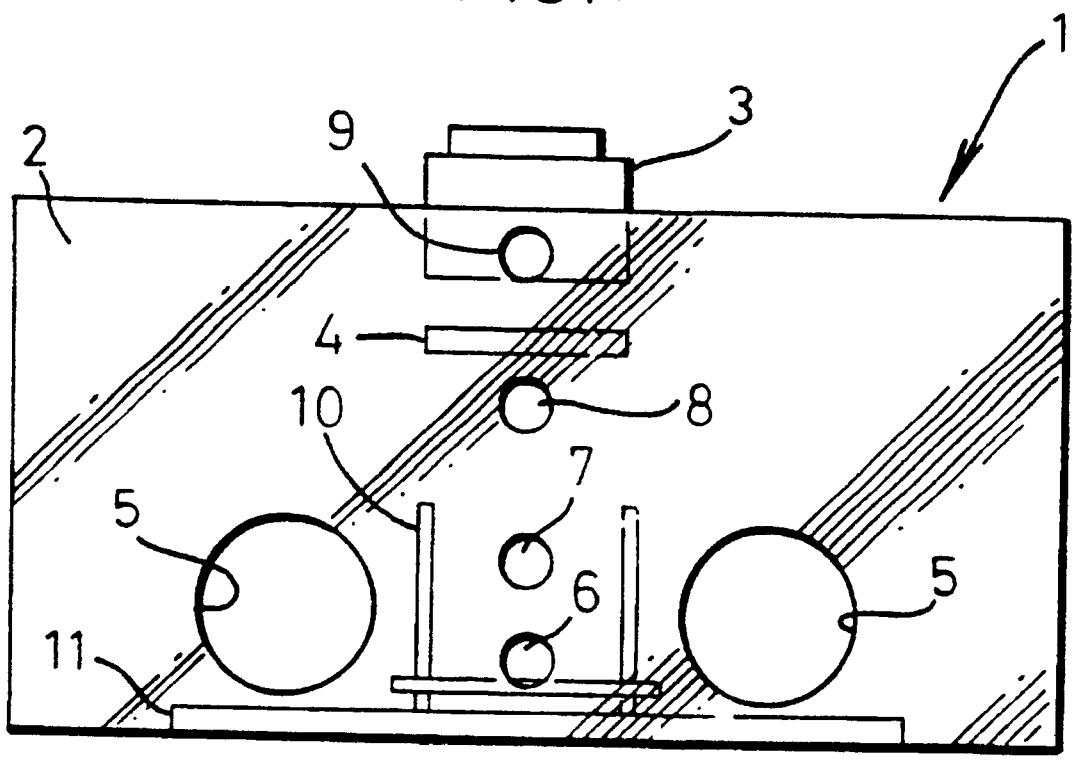
FIG. 1 is a diagrammatic representation of the front elevation of an enclosure for use in one embodiment of the present invention together with diagrammatic representations of commercial devices used with the enclosure in the embodiment.
Figure 1:
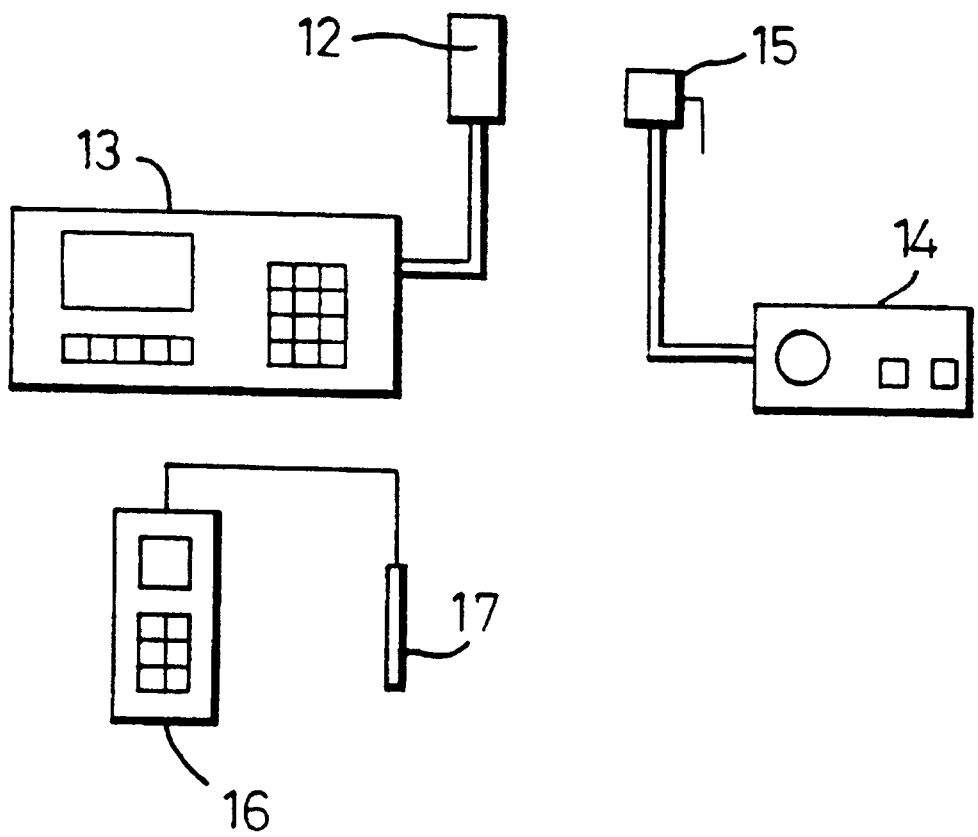

Referring to FIG. 1 the enclosure or dust cabinet (1) for use in the invention is a modified mobile fume cupboard. The side panels are 60 cm×78 cm, the top and bottom panels are 78 cm×100 cm, and the front and back panels are 60 cm×100 cm. The front panel (2), which is transparent, can be slid upwards to allow access to the interior of the cabinet. The cabinet is provided with a top-mounted fan (3). This is a commercially available fan ("Vent-Axia TX71L- "Ventaxia" is a trade mark) connected to a controller (not shown) which allows the fan to be operated at 5 different speeds and in a forward (into the cabinet) or reverse (out of the cabinet) direction. The maximum flow rate is 645 $m^3$/hour. The cabinet has a removable dust carrier (4) having a diameter of 20 cm, which is fixed to die rear panel of the cabinet at a distance of 20 cm from the outlet of the fan within the cabinet. The carrier includes a sieve which has a relatively coarse mesh size, greater than the size of the individual dust particles. Because of the tendency of dust to form loosely bound agglomerates the dust will be retained on the sieve to a considerable extent until air is blown against it by the fan.

The front panel (2) has two holes (5) to allow hands wearing latex gloves to be inserted into the cabinet. The holes are blanked off when not required.

Four smaller holes (6,7,8,9) are provided in a vertical line through the middle of the front panel for the insertion of various proles into the cabinet.

The cabinet as shown in the drawing also contains a support (10) for a nozzle for supporting a compressed air nozzle within the cabinet, and a sample panel (11) which provides a substrate providing test surfaces. The support and the test panel are not present during certain stages of the procedure described below.

The cabinet is connected to three other items of equipment in use, namely an air particle counter (13) with a probe (12), an air compressor (14) with a nozzle (15), and a temperature and humidity meter (16) and a probe (17). The air particle counter may for example be a "Malvern" (trade name) APC 300A.

Testing for uniformity of dust distribution

The ability of the apparatus to ensure even distribution of dust over the test surfaces within the cabinet is confirmed by the following procedure.

In this procedure the support (10) for the compressor nozzle and the test panel (11) are not present.

The cabinet is thoroughly cleaned to remove any residual dust from previous experimental work or natural contamination. Three test papers of equal dimensions are taken and weighed to four decimal places. The test papers are laid at random across the bottom of the cabinet. 1.00 g of household dust is weighed via a sieve on to the dust carrier. The dust had been recovered from domestic vacuum cleaners and filtered through a 106 micrometre mesh to remove large particles and fibres.

The front panel is then lowered and all apertures in the front panel are plugged. The fan mounted in the top panel of the cabinet is then activated (at full speed) so that it draws air into the cabinet to circulate the dust. Circulation is continued for 5 minutes. The fan is then switched off and the dust in the air within the cabinet is then allowed to settle. The cabinet is left for 90 minutes,which is well in excess of the 45 minutes found to be necessary to reach a steady state.

Once the dust is allowed to settle the test surface is examined visually to check that the distribution of dust is visually even. The test papers are carefully removed, taking care that none of the dust collected on them is lost, and are re-weighed to four decimal places. From this the amount of dust collected on each test area can be determined.

The test is repeated a number of times with the test papers being placed in different positions on the bottom of the cabinet.

If the results for the amount of dust collected for each run are within ±5% the distribution is considered to be acceptably uniform.

Preparation of dusted test panel

Sufficient house dust for the entire experiment is filtered and stored in a silica gel dessicator. This ensures that the dust used throughout the experiment is homogeneous, at the same moisture content, and dry enough to prevent agglomeration. For each run 1.00 g dust is used.

A test panel is selected. This panel will be re-cleaned and used for each subsequent test so that the surface conditions will be as close to one another as possible for each product whose effect on dust retention is to be assessed. An example of a suitable test panel is matte-finish medium coloured wood-effect paper laminate on chipboard. This type of material is used in much of the modern furniture on the market. However, depending on the intened use of any product whose effect is to be tested, the test panel could be lacquered wood, plastic or glass.

The test surface is sufficiently large to provide three test surfaces each of 20 cm×30 cm. The panel is thoroughly cleaned, first with water, and then with hydrocarbon solvent to remove any dust, greasy marks, and previous coats of polish. The panel is then marked out into three 30 cm×20 cm areas. The first area is left blank, and products to be tested are applied to the other two areas. Each product is applied directly to a standard cotton duster. The amount of each product applied to the duster is kept as constant as possible, while taking into account any recommended usage instructions. The method of application is kept as constant as possible. The product is applied and wiped 20 times in a standard wipe pattern with even pressure. It is then buffed with a dry side of of the duster a further 20 times.

The test panel is left to stand in a dust free environment for an hour to allow for the evaporation of volatile materials and the levelling of any polish film applied to a test surface. It is then placed in the cabinet in the centre of the bottom panel of the test cabinet, and then coated with dust as described above under "Testing the uniformity of dust distributions."

Testing for the removal of dust from test surfaces

After the dust has been allowed to settle, the front panel of the enclosure is raised and the support for the compressor nozzle is introduced into the cabinet just behind the front panel, taking care not to disturb the dust already deposited on the test panel. The front panel is then lowered to close the enclosure., The probe (12) of the temperature and humidity meter (13) is inserted into aperture (9) in the front panel. The probe (15) of the air particle counter (14) is inserted into aperture (8).

The nozzle support is a retort stand and clamp, and the compressed air nozzle is passed through the lowest central aperture (6) and is clamped, using the access provided by the two apertures (5), so that the air flow is directed downwardly and the nozzle is held about 5 mm above the surface of the bottom panel. The nozzle has a diameter of ca. 7 mm, and is supplied with air at a pressure of 1.5. bar.

The test panel is moved so that the blank test surface is directly under the air compressor nozzle. Once the cabinet is set up, it is left for another hour to allow any disturbed dust to settle. The other two test surfaces are covered with a mask that does not touch the surface on which dust has been dusted.

The background air particle count is measured using the air particle counter. The sample is taken from the cabinet through the probe for one minute at a flow rate of one ft$^3$/min. Three readings are taken and the mean value used to correct the particle count obtained subsequently.

The temperature and humidity are measured, the compressor is activated for 20 seconds, and during this period and for a subsequent 40 seconds a sample of air was taken through the probe to the air particle counter as before.

Once the air particles have been determined the cabinet is left for 20 minutes to reach equilibrium again. The test panel is moved so that the first of the treated areas is below the compressor nozzle. The second treated area, remains masked.

The background air particle count is determined and the air particle count after application of compressed air is determined as before.

The process is repeated for the third test area after a suitable equilibration time.

The measurements of temperature and humidity are made to confirm that measurements of dust levels made at different times are made under comparable atmospheric conditions.

INDUSTRIAL APPLICABILITY

The experimental results obtained have confirmed that the procedure described above is capable of distinguishing the dust retention properties of untreated surfaces from those that have been subjected to various commercial products intended to be applied to hard surfaces. The methodology disclosed herein utilizes readily available components to study atmospheric contents instead of conducting more complex direct surface examination procedures.

What is claimed is:

1. A process for comparing dust retention properties of a first surface of a substrate with the dust retention properties of a second surface of a substrate that comprises, within a dust-retaining enclosure,
    (a) coating the first surface and the second surface with a standardized layer of dust,
    (b) covering the second surface with a shield,
    (c) measuring the quantity of dust particles in the atmosphere within the enclosure,
    (d) subjecting the first surface to a standardized dust dislodging force sufficient to dislodge dust from at least one of the surfaces,
    (e) measuring the quantity of dust particles in the atmosphere within the enclosure and determining any increase in the quantity of dust particles in the atmosphere within the enclosure as a result of the dust dislodging force,
    (f) removing any excess dust particles resulting from the application of the dust dislodging force from the atmosphere in the enclosure,
    (g) measuring the quantity of dust particles in the atmosphere within the enclosure,
    (h) removing the shield from the second surface,
    (i) subjecting the second surface to a standardized dust dislodging force,
    (j) measuring the quantity of dust particles in the atmosphere within the enclosure and determining any increase in the quantity of dust particles in the atmosphere within the enclosure as a result of the dust dislodging force, and
    (k) comparing the relative amounts of dust particles found by steps (e) and (j).

2. The process according to claim 1, wherein the dust dislodging force is provided by a stream of gas.

3. The process according to claim 1, wherein a dust layer is deposited on the surface after the substrate has been introduced into the enclosure.

4. The process according to claim 3 wherein the surfaces are provided on substrates of the same material and at least one of the surfaces has been treated with a material to modify the dust retention properties of the surface.

5. The process according to claim 4, wherein the enclosure is provided with a dust receiving means and air distribution means for passing air over the dust receiving means, and (i) dust is introduced into the dust receiving means, and (ii) the air distribution means is operated so as to pass air over the dust receiving means after the substrate has been introduced into the enclosure.

6. The process according to claim 5, wherein the air distribution means is operated to as to draw air into the enclosure.

7. An apparatus suitable for use in comparing the dust retention properties of surfaces, said apparatus comprising:

(a) a dust retaining enclosure, (b) substrate introduction means for introducing a substrate into the enclosure, said substrate having a surface including at least two surface sections exposed to the atmosphere within the container when within the container, (c) at least one sealable opening in a wall of the enclosure for allowing manipulation of the substrate within the enclosure from outside the enclosure, (d) gas stream means for introducing a stream of gas into the enclosure adjacent to said surface of the substrate, (e) a movable mask for preventing the stream of gas from contacting at least one of the surface sections of the surface of the substrate, and (f) dust measurement means for measuring the dust content in the atmosphere within the enclosure.

8. The apparatus according to claim 7, further comprising a dust distribution means, said dust distribution means comprising a dust receiving means within the enclosure and air distribution means for passing air over the dust receiving means.

* * * * *